Aug. 8, 1961 R. V. SCHREINER Plant Pat. 2,077

IRIS PLANT

Filed Sept. 27, 1960

WITNESS

Addison E. Avery

INVENTOR

ROBERT V. SCHREINER

BY: Rummler and Snow

ATTYS.

United States Patent Office

Plant Pat. 2,077
Patented Aug. 8, 1961

2,077
IRIS PLANT

Robert V. Schreiner, Rte. 2, Box 297, Salem, Oreg.
Filed Sept. 27, 1960, Ser. No. 58,867
1 Claim. (Cl. 47—60)

My present discovery relates to a new and distinct variety of iris plant which was developed from a cross of an unnamed seedling derived from "Carolyn Jane" and "Flying Saucer" (both unpatented) and "Belle Meade" (unpatented). The crosses were made by me at my nursery in Salem, Oregon.

I have asexually reproduced this new variety by division of rhizomes, performed by me at my nursery in Salem, Oregon.

The outstanding features of my new variety are (1) the striking contrast between the snowy white hue characterizing the centers of both the upper petals (standards) and lower petals (falls) and the rich blue-violet margining of both standards and falls, (2) the stylish, swirling, intense, petunia-like ruffling of both standards and falls, not equalled by any other iris plant, and (3) its health, vigor, and freedom from disease.

My new variety of iris plant is shown in full color in the accompanying drawing in which.

Figure 1:
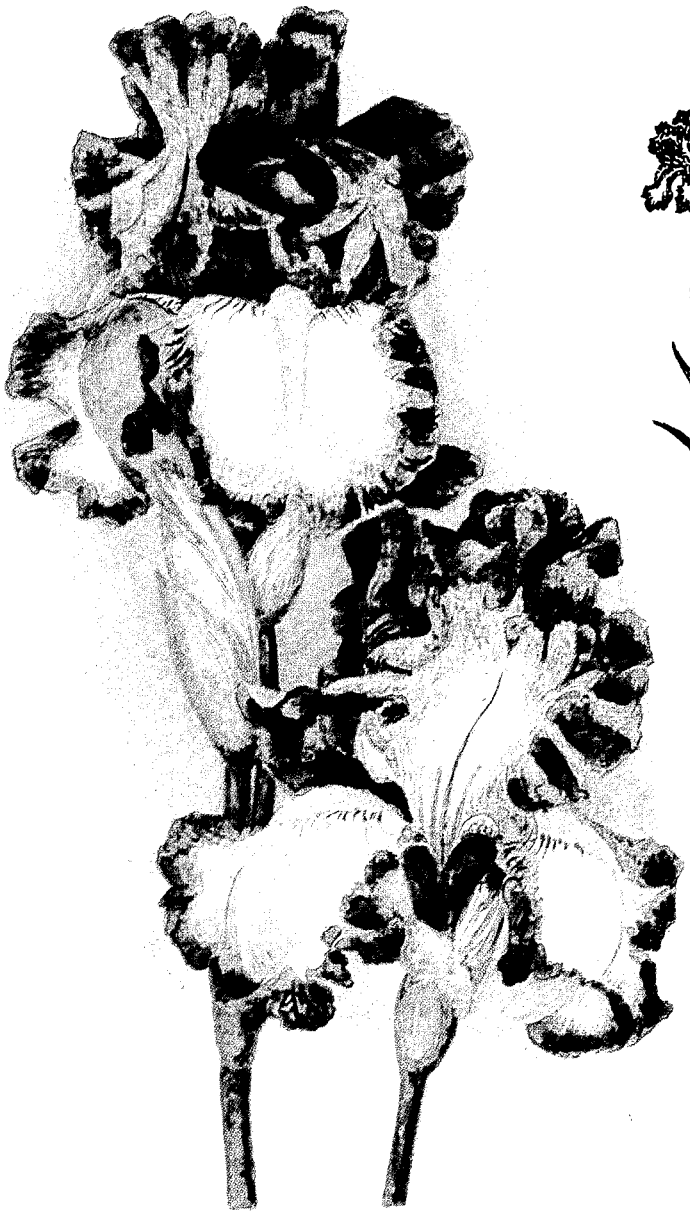
FIGURE 1 illustrates a portion of the stem with a bud and two open flowers.
Figure 2:
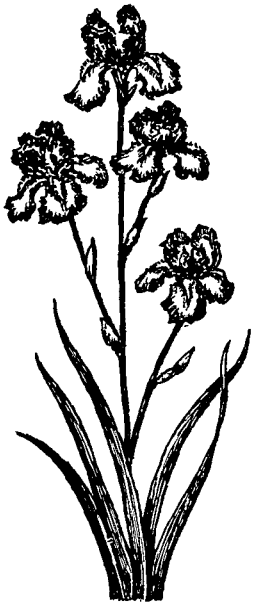
FIG. 2 is a pen and ink sketch illustrating the stalk and candelabrum branching.

In the following detailed description, color plate references indicate Ridgeway's Color Standards and Nomenclature, while other color names refer to the ordinary dictionary meaning of the terms.

*Plant*

Growth habit: Vigorous; stems rigid and moderately branched. Form: foliage grows in mound form.

Propagation: Variety propagates easily by division of rhizomes, and at a good rate of reproduction.

Blooming habit: Blooms early-midseason. Plants are floriferous and blooms are long-lasting. Each stem (with its side branches) may bear 10–12 buds and blossoms. Individual blossoms last three days, and a single stem will carry open blooms continuously for a period of approximately 2½ weeks.

Disease resistance: Foliage is healthy and exceptionally free from leafspot; rhizomes are firm and resistant to rot caused by unfavorable weather conditions. Trials of the new variety have been conducted in Salem, Marion County, Oregon, in extreme variable weather, some most apt to promote excessive leafspot and rot. The new variety has been carefully tested and observed for several years with respect to its growing habits and its resistance to leafspot, and the rhizomes to rot. The results of these trials and tests have demonstrated that the beforementioned qualities of the new variety are firmly fixed and that resistance to leafspot and rot is inherent in the new variety.

Stems: Deep green, approximately midway between Dark Dull Yellow-Green (Plate XXXII) and Deep Dull Yellow-Green (Plate XXXII); strong and straight, rising upright to about 36 inches; much branched, with side branches ranging from 12 inches in length on lower part of stem to 6 to 7 inches on upper part of stem.

Foliage:

*Height.*—Rising in mound form, the foliage averages approximately 25 inches in height.

*Color.*—Medium green, approximately Cress Green (Plate XXXII). Retention of foliage color is good throughout the growing season until late fall.

*Flower*

Bud:

*Size.*—Approximately 1 to 1¼ inches long when color first shows, expanding rapidly so that the day before emergence into flower, buds are from three to four inches in length.

*Opening.*—Bud grows imperceptibly for several days, then develops rapidly after color begins to show.

*Color.*—White with Dark Soft Blue-Violet (Plate XXIII) tip. Enclosure (spathe) is light green, the papery portion being Vinaceous-Buff (Plate XL) to Avellaneous (Plate XL).

Bloom:

*Size.*—Large, measuring approximately 7 inches from top to bottom and 6 inches from side to side.

*Form.*—Classical, modified flaring form; upper petals are cupped and firmly held in place. Lower petals are semi-flaring. Both upper petals (standards) and lower petals (falls) are intensely frilled, the frilling, which resembles that seen in giant petunias, extending in from the edges of the petals approximately ½ inch.

*Substance.*—Heavy, with excellent capacity to withstand wind, rain, and extremes of heat. The heavy substance is retained during the life of the flower.

*Aspect.*—Sparkling, shining texture enhances the clean, contrasting plicata color pattern, here revealed in snowy white ground broadly margined rich soft blue-violet.

*Keeping qualities.*—Each flower lasts three days, and a single stem with its side branches will have flowers for approximately 2½ weeks.

*Color.*—Both upper petals (standards) and lower petals (falls) exhibit a pure white ground color surrounded by a ½ inch margining of soft rich blue-violet, approximately Dark Soft Blue-Violet (Plate XXIII). This margining is approximately co-terminous with the ruffling or frilling, both being about ½ inch wide. Between the white ground color and blue-violet margining is a transition zone approximately ¼ inch wide characterized by a subtle stippling and fine traceries of blue-violet on white. Occasionally transitional touches of frilling originate in this transitional color zone. The three style arms (center of flower) are the same shade of Dark Soft Blue-Violet (Plate XXIII) as the margining. The beard is white, gradually deepening to cream and finally to pale yellow in the depth of the flower.

*Fragrance.*—Mild.

*Form of petals.*—Upper petals or standards are broadly arching; lower petals or falls are of modified flare form. Both upper and lower petals have the most intense ruffling or frilling observed in any iris by me. They are ruffled or frilled, however, rather than crinkled. The frilling is the swirling type most commonly seen in giant frilled petunias.

*Size of petals.*—Both standards and falls are approximately 4 inches from claw to tip.

Genital organs:

*Pistil.*—Style arms, three; blue- violet.

*Stamens.*—Filaments, three; measure approximately 1⅞ inches long. Anther approximately ¾ inch long; color—light yellow.

*Pollen.*—Creamy white; fertile.

*Comparison*

The two varieties most like my new variety are "Belle Meade" and "Bright Contrast" (both unpatented). The principal differences are as follows:

My new variety has far more intense ruffling or frilling than either "Belle Meade," which is only lightly ruffled, or "Bright Contrast," which is only slightly waved.

The margining of my new variety is a slightly deeper tone of blue-violet than the margining of "Belle Meade," thus intensifying the contrast between the white ground color and blue-violet margining.

The upper petals (standards) of my new variety exhibit a central zone of pure white, as do the lower petals (falls). In contrast the upper petals of "Belle Meade" are an almost solid blue-violet color with some white mottling near the center.

The margining of my new variety is much bluer than the margining of "Bright Contrast," which is purple.

The upper petals of my new variety exhibit a large pure white central zone that is always present. In contrast the upper petals of "Bright Contrast" are an almost solid purple color with a variable slight mottling of white near the center.

Having thus disclosed my invention, I claim:

A new and distinct variety of iris plant, substantially as herein shown and described, characterized particularly by the extremely stylish ruffling or frilling of its blooms; by the brilliance of the contrast between the snowy white ground color of both its standards and its falls and the vivid blue-violet margining; by its excellent health and abundance of bloom; ease of propagation; and the heavy texture of the bloom which resists the elements.

No references cited.